(12) United States Patent
Wang et al.

(10) Patent No.: US 12,004,897 B2
(45) Date of Patent: Jun. 11, 2024

(54) QUANTITATIVE ANALYSIS METHOD FOR CARDIAC MOTION, AND ULTRASONIC SYSTEM

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventors: Bo Wang, Shenzhen (CN); Longfei Cong, Shenzhen (CN); Lei Zhu, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 416 days.

(21) Appl. No.: 17/237,868

(22) Filed: Apr. 22, 2021

(65) Prior Publication Data

US 2021/0321974 A1 Oct. 21, 2021

Related U.S. Application Data

(63) Continuation of application No. PCT/CN2018/111446, filed on Oct. 23, 2018.

(51) Int. Cl.
*A61B 8/02* (2006.01)
*A61B 8/00* (2006.01)
*A61B 8/08* (2006.01)

(52) U.S. Cl.
CPC .............. *A61B 8/02* (2013.01); *A61B 8/0833* (2013.01); *A61B 8/465* (2013.01); *A61B 8/469* (2013.01)

(58) Field of Classification Search
CPC ......... A61B 8/02; A61B 8/0833; A61B 8/465; A61B 8/469
See application file for complete search history.

(56) References Cited

U.S. PATENT DOCUMENTS

| 7,722,540 B2 | 5/2010 | Abe et al. |
| 8,343,052 B2 | 1/2013 | Kawagishi et al. |

(Continued)

FOREIGN PATENT DOCUMENTS

| CN | 1895176 A | 1/2007 |
| CN | 101152096 A | 4/2008 |

(Continued)

OTHER PUBLICATIONS

PCT International Preliminary Report on Patentability dated May 6, 2021, issued in related International Application No. PCT/CN2018/111446, with English translation (12 pages).

(Continued)

*Primary Examiner* — Dixomara Vargas
(74) *Attorney, Agent, or Firm* — Sheppard Mullin Richter & Hampton LLP (57) ABSTRACT

A quantitative analysis method for cardiac motion, and an ultrasonic system, said method comprising: emitting an ultrasonic wave to a target heart; receiving an ultrasonic echo returned from the target heart; determining an ultrasonic image of the target heart according to the ultrasonic echo; acquiring an area of interest in the ultrasonic image; and tracking the motion of the area of interest, so as to acquire torsion parameters of the target heart and the confidence of the torsion parameters. The present invention performs quantitative analysis on the torsion motion of the heart, and also provides the confidence of the analysis result, that is, quantitative evaluation is also performed on the (Continued)

analysis result, assisting the physician in making a more accurate cardiac function evaluation.

18 Claims, 4 Drawing Sheets

(56) References Cited

U.S. PATENT DOCUMENTS

| | | | |
|---|---|---|---|
| 8,454,514 B2 | 6/2013 | Kawagishi et al. | |
| 9,138,200 B2 | 9/2015 | Abe | |
| 9,629,615 B1* | 4/2017 | Tavakoli | A61B 8/0883 |
| 10,413,733 B2* | 9/2019 | Mi | A61B 5/29 |
| 10,792,009 B2* | 10/2020 | Ohuchi | A61B 8/08 |
| 2007/0167809 A1* | 7/2007 | Dala-Krishna | A61B 8/13 600/459 |
| 2009/0198298 A1* | 8/2009 | Kaiser | A61N 1/3686 607/17 |
| 2011/0249005 A1* | 10/2011 | Hautvast | G06T 11/206 345/440 |
| 2012/0078097 A1* | 3/2012 | Wang | A61B 8/0883 600/437 |
| 2012/0243761 A1* | 9/2012 | Senzig | A61B 6/5217 378/19 |
| 2012/0302870 A1* | 11/2012 | Bjallmark | A61B 8/0883 600/443 |
| 2013/0211256 A1* | 8/2013 | Russell | G16H 50/30 600/407 |
| 2013/0336558 A1* | 12/2013 | Manzke | A61B 6/5235 382/128 |
| 2015/0094584 A1* | 4/2015 | Abe | A61B 8/483 600/443 |
| 2015/0130901 A1 | 5/2015 | Sornes | |
| 2015/0173707 A1* | 6/2015 | Ohuchi | G06T 19/20 600/443 |
| 2015/0272547 A1* | 10/2015 | Freiburger | A61B 8/52 600/438 |
| 2015/0327780 A1* | 11/2015 | Kano | A61B 90/37 600/407 |
| 2015/0335308 A1* | 11/2015 | Pedrizzetti | A61B 8/5207 600/454 |
| 2015/0371437 A1* | 12/2015 | Mansi | G06T 11/60 382/131 |
| 2016/0220152 A1* | 8/2016 | Meriheinä | A61B 5/746 |
| 2017/0215807 A1* | 8/2017 | Lundback | A61B 5/7264 |
| 2018/0101644 A1 | 4/2018 | Hammes et al. | |
| 2018/0249979 A1* | 9/2018 | Wang | A61B 5/055 |
| 2019/0343482 A1* | 11/2019 | Abe | A61B 8/085 |

FOREIGN PATENT DOCUMENTS

| | | |
|---|---|---|
| CN | 101484074 A | 7/2009 |
| CN | 101658433 A | 3/2010 |
| CN | 107913076 A | 4/2018 |

OTHER PUBLICATIONS

First Search dated Apr. 23, 2022, issued in related Chinese Application No. 201880097298.9 (3 pages).

PCT International Search Report and the Written Opinion dated Jun. 27, 2019, issued in related International Application No. PCT/CN2018/111446, with partial English translation (10 pages).

* cited by examiner

QUANTITATIVE ANALYSIS METHOD FOR CARDIAC MOTION, AND ULTRASONIC SYSTEM

This application is a continuation application of International Patent Application No. PCT/CN2018/111446, filed with the State Intellectual Property Office (SIPO) of the People's Republic of China on Oct. 23, 2018. The entire content of the above-referenced application is incorporated herein by reference.

TECHNICAL FIELD

The disclosure relates to a quantitative analysis method for cardiac motion, and an ultrasonic system.

BACKGROUND

An important branch discipline of clinical medicine is cardiovasology. With the continuous development of cardiovasology, methods for diagnosis of cardiovascular diseases, no matter whether they are noninvasive methods or invasive methods, have constantly emerged, changed, and improved.

An echocardiography is a method developed in the 1950s to diagnose cardiovascular diseases. The echocardiography technology is essentially an ultrasound imaging technology, which is a noninvasive imaging technology and has the advantages of being easy and simple to operate and having strong repeatability. The echocardiography may not only display anatomical images of the heart and great vessels, but also may observe physiological activities of the heart and great vessels in real time, providing valuable diagnostic data. Thus, the technology has attracted much attention of clinicians, and has been continuously popularized and applied. The echocardiography technology has developed rapidly, starting from an M-mode echocardiography to a two-dimensional echocardiography, a transesophageal echocardiography, etc.

In addition, technologies for quantitative analysis of cardiac motion have also emerged, typically such as Doppler echocardiography (TDI) and speckle tracking based on an ultrasound image (such as a B-mode image), which are briefly described below.

In the Doppler echocardiography technology, a motion velocity of tissues in the direction of an acoustic beam is measured by using the principle of a Doppler frequency shift, which can provide an effective means for analysis of cardiac motion. However, due to the limitation of the Doppler principle, in the Doppler echocardiography technology, two-dimensional velocity information of the heart in an imaging plane cannot be accurately obtained, which limits the application of the Doppler echocardiography technology to some extent.

In the speckle tracking based on a B-mode image, a position of the same ultrasound speckle in a two-dimensional B-mode ultrasound image is tracked, so as to determine a positional change relationship of a corresponding myocardial tissue. When motion displacement and deformation of the tissue are small, it can be approximately considered that a speckle pattern of the tissue remains fixed. Therefore, motion tracking and quantitative measurement of the specific tissue can be implemented by tracking the motion of the specific speckle in the B-mode ultrasound image. Because the speckle tracking based on a B-mode ultrasound image is used to track the motion of the myocardial tissue by tracking speckles formed by echo signals of the cardiac tissue on the B-mode ultrasound image, the technology may obtain the two-dimensional motion of the cardiac tissue in the imaging plane and may be applied to various sections of heart views. Specifically, the speckle tracking can be used to accurately and quantitatively analyze motion of various parts of the heart. Ultrasound speckles at different positions (such as endocardium, epicardium and myocardium) of the heart are tracked, such that motion situations, such as speed, displacement and deformation, of tissue structures corresponding to the ultrasound speckles can be obtained, and physiological characteristics of the heart tissue can be quantitatively analyzed by using the information. For example, for patients with cardiovascular obstruction, the range of motion of a blood supply part of an obstructed blood vessel will be lower than that of a normal blood supply part, which is embodied during the cardiac motion process in that, the motion of the part affected by the obstructed blood vessel is passive motion (motion drawn by the motion of surrounding tissues). Therefore, some motion parameters such as deformation, strain, and a strain rate will be obviously abnormal. The speckle tracking can be used to calculate motion parameters of different parts of the heart by accurately measuring motion situations of the heart, so as to locate an abnormal part of the heart, which provides clinical diagnosis significance for users.

SUMMARY

Considering that in the prior art, accuracy and reliability of motion parameters obtained by tracking speckles of the heart are neglected in most researches, the disclosure provides a quantitative analysis method for cardiac motion, and an ultrasonic system, to improve the accuracy of quantitative analysis of cardiac motion.

In one embodiment, an embodiment provides a quantitative analysis method for cardiac motion, which may include:
  transmitting an ultrasonic wave to a target heart;
  receiving an ultrasonic echo returned from the target heart;
  determining an ultrasound image of the target heart according to the ultrasonic echo;
  obtaining a region of interest in the ultrasound image; and
  performing motion tracking on the region of interest, so as to obtain a torsion parameter of the target heart and a reliability of the torsion parameter.

In an embodiment, the quantitative analysis method for cardiac motion further includes: displaying the torsion parameter and the reliability of the torsion parameter.

In an embodiment, the quantitative analysis method for cardiac motion further includes: displaying the ultrasound image and the region of interest.

In an embodiment, performing motion tracking on the region of interest, so as to obtain a torsion parameter of the target heart includes:
  determining speckles in the region of interest; and
  performing motion tracking on the speckles to obtain the torsion parameter of the target heart.

In an embodiment, the torsion parameter includes a rotation parameter of a preset segment.

In an embodiment, performing motion tracking on the region of interest, so as to obtain a reliability of the torsion parameter includes:
  determining speckles in the preset segment in the region of interest;
  performing motion tracking on the speckles to obtain image quality and a tracking result corresponding to the preset segment; and determining a reliability of the rotation parameter of the preset segment according to the image quality and the tracking result corresponding to the preset segment.

In an embodiment, displaying the torsion parameter includes:

displaying the rotation parameter of the preset segment in the form of a curve graph, where the preset segment is identified in the curve graph by at least one of a color, a pattern, and a character.

In an embodiment, displaying the reliability of the torsion parameter includes:

displaying a structure icon corresponding to the preset segment, where the preset segment is identified in the structure icon by at least one of a color, a pattern, and a character; and displaying a reliability of the rotation parameter of the preset segment on the structure icon.

In an embodiment, displaying the reliability of the rotation parameter of the preset segment on the structure icon includes:

displaying the reliability of the rotation parameter of the preset segment on a boundary of the structure icon corresponding to the preset segment by at least one of a color, a pattern, and a character.

In an embodiment, the quantitative analysis method for cardiac motion further includes:

receiving a segment selection instruction for the preset segment corresponding to the structure icon;

determining a selected segment according to the segment selection instruction; and highlighting the selected segment on the structure icon.

In an embodiment, the quantitative analysis method for cardiac motion further includes: highlighting a rotation parameter of the selected segment on the curve graph.

In an embodiment, the quantitative analysis method for cardiac motion further includes: highlighting the selected segment in a corresponding region of interest in the ultrasound image.

In an embodiment, highlighting the selected segment on the structure icon includes:

highlighting the selected segment on the structure icon in a highlighted and/or bold manner; or displaying the selected segment and hiding an unselected segment.

In an embodiment, highlighting the rotation parameter of the selected segment on the curve graph includes:

highlighting a rotation parameter curve of the selected segment in a highlighted and/or bold manner; or displaying a rotation parameter curve of the selected segment and hiding a rotation parameter curve of an unselected segment.

In an embodiment, highlighting the selected segment in the region of interest in the ultrasound image includes:

highlighting the selected segment in a corresponding region of interest in the ultrasound image in a highlighted and/or bold manner; or displaying speckles in the region of interest in the ultrasound image corresponding to the selected segment and hiding speckles in the region of interest in the ultrasound image corresponding to an unselected segment.

In an embodiment, displaying the torsion parameter and the reliability of the torsion parameter includes: displaying the rotation parameter of the preset segment and a reliability of the rotation parameter of the preset segment by using a bull's eye plot.

In an embodiment, the quantitative analysis method for cardiac motion further includes: displaying, by using a bull's eye plot, a peak value of the rotation parameter of the preset segment and/or a time spent for the rotation parameter of the preset segment to reach the peak value.

In an embodiment, the torsion parameter includes a left ventricular torsion parameter, where the left ventricular torsion parameter is obtained based on the rotation parameter of the preset segment, and a reliability of the left ventricular torsion parameter is obtained based on the reliability of the rotation parameter of the preset segment.

In an embodiment, the displaying the torsion parameter and the reliability of the torsion parameter includes: displaying rotation parameters of all preset segments and reliabilities of the rotation parameters of all the preset segments by using a curve graph.

In an embodiment, the quantitative analysis method for cardiac motion further includes:

receiving an invalidation selection instruction for the preset segments;

removing a selected invalid segments from the preset segments according to the invalidation selection instruction; and displaying a rotation parameter of a valid segment and a reliability of the rotation parameter of the valid segment using a curve graph, where the valid segment a segment of the preset segments other than the selected invalid segment.

In an embodiment, an ultrasonic system is provided, which may include:

an ultrasonic probe;

a transmitting/receiving control circuit configured to control the ultrasonic probe to transmit an ultrasonic wave to a target heart and receive an ultrasonic echo returned from the target heart; and a processor configured to determine an ultrasound image of the target heart according to the ultrasonic echo; obtain a region of interest in the ultrasound image; and perform motion tracking on the region of interest, so as to obtain torsion parameters of the target heart and a reliability of the torsion parameters.

In an embodiment, the ultrasonic system further includes a display configured to display the torsion parameter and the reliability of the torsion parameter; and/or display the ultrasound image and the region of interest.

In an embodiment, the processor performing the motion tracking on the region of interest so as to obtain the torsion parameter of the target heart includes: determining speckles in the region of interest; and performing the motion tracking on the speckles to obtain the torsion parameter of the target heart.

In an embodiment, the torsion parameter includes a rotation parameter of a preset segment.

In an embodiment, the processor performing the motion tracking on the region of interest so as to obtain the reliability of the torsion parameter includes:

determining speckles in the preset segment in the region of interest;

performing motion tracking on the speckles to obtain image quality and a tracking result corresponding to the preset segment; and determining a reliability of the rotation parameter of the preset segment according to the image quality and the tracking result corresponding to the preset segment.

In an embodiment, the display displaying the torsion parameter includes: displaying the rotation parameter of the preset segment in the form of a curve graph, where the preset segment is identified in the curve graph by at least one of a color, a pattern, and a character.

In an embodiment, the display displaying the reliability of the torsion parameter includes:
  displaying a structure icon corresponding to the preset segment, where the preset segment is identified in the structure icon by at least one of a color, a pattern, and a character; and
  displaying a reliability of the rotation parameter of the preset segment on the structure icon.

In an embodiment, the display displaying the reliability of the rotation parameter of the preset segment on the structure icon includes: displaying the reliability of the rotation parameter of the preset segment on a boundary of the structure icon corresponding to the preset segment by at least one of a color, a pattern, and a character.

In an embodiment, the processor is further configured to receive a segment selection instruction for the preset segment corresponding to the structure icon, and determine a selected segment according to the segment selection instruction; and the display highlights the selected segment on the structure icon.

In an embodiment, the display further highlights a rotation parameter of the selected segment on the curve graph.

In an embodiment, the display further highlights the selected segment in the region of interest in the ultrasound image.

In an embodiment, the display highlighting the selected segment on the structure icon includes:
  highlighting the selected segment on the structure icon in a highlighted and/or bold manner; or
  displaying the selected segment and hiding an unselected segment.

In an embodiment, the display highlighting the rotation parameter of the selected segment on the curve graph includes:
  highlighting a rotation parameter curve of the selected segment in a highlighted and/or bold manner; or
  displaying a rotation parameter curve of the selected segment and hiding a rotation parameter curve of an unselected segment.

In an embodiment, the display highlighting the selected segment in the region of interest in the ultrasound image includes:
  highlighting the selected segment in a corresponding region of interest in the ultrasound image in a highlighted and/or bold manner; or
  displaying speckles in the region of interest in the ultrasound image corresponding to the selected segment and hiding speckles in the region of interest in the ultrasound image corresponding to an unselected segment.

In an embodiment, the display displaying the torsion parameter and the reliability of the torsion parameter includes: displaying the rotation parameter of the preset segment and a reliability of the rotation parameter of the preset segment with a bull's eye plot.

In an embodiment, the display further displays, with a bull's eye plot, a peak value of the rotation parameter of the preset segment and/or a time spent for the rotation parameter of the preset segment to reach the peak value.

In an embodiment, the torsion parameter includes a left ventricular torsion parameter, where the left ventricular torsion parameter is obtained based on the rotation parameter of the preset segment, and a reliability of the left ventricular torsion parameter is obtained based on the reliability of the rotation parameter of the preset segment.

In an embodiment, the display displaying the torsion parameter and the reliability of the torsion parameter includes: displaying rotation parameters of all preset segments and reliabilities of the rotation parameters of all the preset segments by using a curve graph.

In an embodiment, the processor further receives an invalidation selection instruction for the preset segments, and removes a selected invalid segment from the preset segments according to the invalidation selection instruction; and the display displays a rotation parameter of a valid segment and a reliability of the rotation parameter of the valid segment using a curve graph, where the valid segment is a segment of the preset segments other than the selected invalid segment.

In an embodiment, a computer-readable storage medium is provided, which may include a program that can be executed by a processor to implement the quantitative analysis method for cardiac motion described in any one of the embodiments of the disclosure.

According to the quantitative analysis method for cardiac motion, the ultrasonic system and the computer-readable storage medium implemented above, an ultrasonic wave is transmitted to a target heart; an ultrasonic echo returned from the target heart is received; an ultrasound image of the target heart is determined according to the ultrasonic echo; a region of interest in the ultrasound image is obtained; and motion tracking is performed on the region of interest, so as to obtain a torsion parameter of the target heart and a reliability of the torsion parameter. In the disclosure, during the quantitative analysis of the torsional motion of the heart, the reliability of the analysis result is also provided, that is, quantitative evaluation is also performed on the analysis result, which may assist a physician in making a more accurate cardiac function evaluation.

DESCRIPTION OF THE EMBODIMENTS

The disclosure will be further described in detail below through specific implementations in conjunction with the accompanying drawings. Associated similar element reference numerals are used for similar elements in different implementations. In the following embodiments, many details are described such that the disclosure may be better understood. However, it may be effortlessly appreciated by a person skilled in the art that some of the features can be omitted, or can be substituted by other elements, materials, and methods in different cases. In certain cases, some operations involved in the disclosure are not displayed or described in the description, which is to prevent a core part of the disclosure from being obscured by too much description. Moreover, for a person skilled in the art, the detailed description of the involved operations is not necessary, and the involved operations can be thoroughly understood according to the description in the specification and general technical knowledge in the art.

In addition, the characteristics, operations, or features described in the description may be combined in any appropriate manner to form various embodiments. Meanwhile, the steps or actions in the method description may also be exchanged or adjusted in order in a way that is obvious to a person skilled in the art. Therefore, the various orders in the description and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish described objects, and do not have any sequential or technical meaning. Moreover, as used in the disclosure, "connection" or "coupling", unless otherwise stated, comprises both direct and indirect connections (couplings).

Cardiac motion is described first.

The cardiac motion usually includes systolic, diastolic, and torsional motion. For a long time, there have been many studies on the systolic and diastolic motion of the heart, and the understanding is also relatively sufficient. However, there are relatively few studies on the torsional motion of the heart.

The torsional motion of the heart is defined as the motion of the left ventricular apex and the basal part in opposite rotational directions, including torsion and detorsion. The torsional motion of the heart was pioneered by the physiologist William Harvey. Since William Harvey first proposed the concept of left ventricular torsional motion in 1628, people began to study the torsional motion of the heart gradually. Currently, many experiments have proved that left ventricular torsional motion plays an important role in ejection and filling of the left ventricle. Measuring the left ventricular torsional motion is particularly important to evaluating cardiac function changes and providing local and global information of cardiac muscles, which is beneficial to early diagnosis and treatment of cardiovascular diseases.

In the disclosure, quantitative analysis is performed on cardiac motion based on speckle tracking to obtain torsion parameters of a heart. For example, the torsion parameters of the heart can be obtained through analysis by measuring motion on two heart sections, i.e., an apex and a base, based on speckle tracking. However, in the process of quantitative analysis of cardiac motion based on speckle tracking, the analysis accuracy is directly affected by the tracking accuracy. The speckle tracking of a two-dimensional echocardiography is taken as an example. Due to imaging conditions such as acoustic windows, the two-dimensional echocardiography sometimes has local signal defects, noise, and artifacts, which will severely affect a tracking algorithm and lead to inaccurate local tracking. In this case, motion parameters obtained are inevitably not accurate, not credible, and not reliable.

Therefore, the applicant proposed that it is necessary to visually and comprehensively evaluate the quality of tracking, for example, to quantitatively evaluate the reliability and accuracy of motion parameters by introducing a reliability, which is of great significance in the field of quantitative cardiac analysis and can greatly affect the application of this technology in clinical and scientific research fields.

Figure 1:
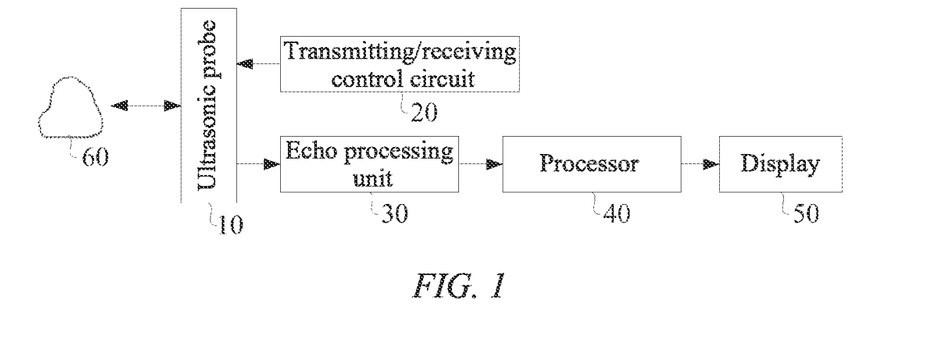
FIG. 1 is a schematic structural diagram of an ultrasonic system according to an embodiment.

FIG. 1 is a schematic structural diagram of an ultrasonic system according to an embodiment. The ultrasonic system may comprise an ultrasonic probe 10, a transmitting/receiving control circuit 20, an echo processing unit 30, and a processor 40. In an embodiment, the ultrasonic system may further comprise a display 50. Details will be described below.

The ultrasonic probe 10 comprises a plurality of array elements, which are used to implement mutual conversion of an electric pulse signal and an ultrasonic wave, so as to transmit an ultrasonic wave to a biological tissue 60 (e.g., a biological tissue in a human or animal body) to be detected and receive an ultrasonic echo reflected by the tissue. The plurality of array elements included in the ultrasonic probe 10 may be arranged into a row to form a linear array, or arranged into a two-dimensional matrix to form an area array; or the plurality of array elements may form a convex array. The array element may transmit an ultrasonic wave according to an excitation electrical signal, or convert a received ultrasonic wave into an electrical signal. Therefore, each of the array elements may be used to transmit an ultrasonic wave to a region of interest of a biological tissue, and may also be used to receive an ultrasonic echo returned from the tissue. During ultrasound detection, a transmitting sequence and a receiving sequence may be used to control which array elements are used to transmit an ultrasonic wave and which array elements are used to receive an ultrasonic wave, or control the array elements to be used to transmit an ultrasonic wave or receive an ultrasonic echo in different slots. All the array elements participating in ultrasound transmission can be simultaneously excited by the electrical signal, so as to simultaneously transmit the ultrasonic wave; or the array elements participating in ultrasound transmission may be excited by several electrical signals with a specific time interval, so as to continuously transmit ultrasonic waves with a specific time interval.

The transmitting/receiving control circuit 20 is configured to control the ultrasonic probe 10 to transmit an ultrasound beam to the biological tissue 60, and also to control the ultrasonic probe 10 to receive an ultrasonic echo that corresponds to the ultrasound beam and is reflected by the tissue. In a specific embodiment, the transmitting/receiving control circuit 20 is configured to generate a transmitting sequence and a receiving sequence, and output them to the ultrasonic probe. The transmitting sequence is used to control some or all of the plurality of array elements in the ultrasonic probe 10 to transmit an ultrasonic wave to a target of interest in the biological tissue 60. Parameters of the transmitting sequence comprise the number of array elements used for transmission and ultrasonic transmission parameters (such as amplitude, frequency, the number of wave transmissions, a transmission interval, a transmission angle, a wave mode, and/or a focus position). The receiving sequence is used to control some or all of the plurality of array elements to receive an echo that corresponds to the ultrasonic wave and is reflected by the tissue. Parameters of the receiving sequence comprise the number of array elements used for receiving and echo receiving parameters (such as a receiving angle and depth). For different purposes of the ultrasonic echo or different images generated based on the ultrasonic echo, the ultrasonic parameters in the transmitting sequence and the echo parameters in the receiving sequence are also different.

The echo processing unit 30 is configured to process an ultrasonic echo signal received by the ultrasonic probe 10, for example, to perform processing such as filtering, amplification, and beam synthesis on the ultrasonic echo signal to obtain ultrasonic echo data. In a specific embodiment, the echo processing unit 30 may output the ultrasonic echo data to the processor 40; or the echo processing unit 30 may first store the ultrasonic echo data in a memory, and when calculation needs to be performed on the basis of the ultrasonic echo data, the processor 40 reads the ultrasonic echo data from the memory. Those skilled in the art should understand that, in some embodiments, when processing such as filtering, amplification, and beam synthesis does not need to be performed on the ultrasonic echo signal, the echo processing unit 30 may also be omitted.

The processor 40 is configured to obtain ultrasonic echo data, and use a related algorithm to obtain a desired parameter or image.

The display 50 may be configured to display information, for example, to display the parameter, the image, etc. calculated by the processor 40. Those skilled in the art should understand that, in some embodiments, the ultrasonic system itself may not be integrated with the display, but is connected to a computer device (such as a computer), and displays information by means of a display (such as a display screen) of the computer device.

The above is some descriptions of the structure of the ultrasonic system. In an embodiment of the disclosure, the ultrasonic system performs quantitative analysis on a heart. For example, the transmitting/receiving control circuit 20 controls the ultrasonic probe 10 to transmit an ultrasonic wave to a target heart and receive an ultrasonic echo returned from the target heart; and the processor 40 determines an ultrasound image of the target heart according to the ultrasonic echo, then obtains a region of interest in the ultrasound image, and performs motion tracking on the region of interest, so as to obtain a torsion parameter of the target heart and a reliability of the torsion parameter. The region of interest may include the endocardium, epicardium, myocardium, etc. The region of interest may be preset or may be input by a user. For example, the user selects the region of interest in the ultrasound image by using a mouse, a keyboard, etc. In an embodiment, that the processor 40 performs motion tracking on the region of interest to obtain a torsion parameter of the target heart may be implemented based on speckle tracking. For example, the processor 40 determines speckles in the region of interest, and then performs motion tracking on the speckles to obtain the torsion parameter of the target heart. In an embodiment, the display 50 may display one or both of the following (1) and (2): (1) the ultrasound image and the region of interest determined by the processor 40; and (2) the torsion parameter and the reliability of the torsion parameter.

The following describes the torsion parameter of the heart and the reliability thereof.

The torsion parameter of the heart is a parameter about the torsional motion of the heart. In an embodiment, the torsion parameter of the heart may comprise a global torsion parameter and/or a local torsion parameter. The global torsion parameter is a parameter used to globally describe the torsional motion of the heart, such as a left ventricular torsion parameter. The local torsion parameter is a parameter used to describe the torsional motion of the heart from various parts of the heart, such as a rotation parameter of a preset segment. The preset segment of the heart may comply with the division of standard segments defined by an ultrasound industry standards association, or may be defined by a user himself or herself. In an embodiment, the left ventricular torsion parameter may be obtained based on a rotation parameter of the preset segment. For example, the left ventricular torsion parameter may be obtained based on rotation parameters of two segments, i.e., the apex and the base.

The reliability of the torsion parameter of the heart is used to quantify the reliability and accuracy of the torsion parameter. The torsion parameter of the heart comprises the global torsion parameter and/or the local torsion parameter, and accordingly, the reliability of the torsion parameter of the heart may comprise a reliability for quantitative evaluation of the global torsion parameter and a reliability for quantitative evaluation of the local torsion parameter, such as a reliability of the left ventricular torsion parameter and/or a reliability of the rotation parameter of preset segment. In an embodiment, the reliability of the left ventricular torsion parameter is obtained based on a reliability of the rotation parameter of the preset segment. For example, the reliability of the left ventricular torsion parameter may be obtained based on the reliability of the rotation parameters of the two segments, i.e., the apex and the base.

The following describes the calculation and display of the rotation parameter of the preset segment of the heart and the reliability of the rotation parameter.

In an embodiment, the performing, by the processor 40, motion tracking on the region of interest, so as to obtain a torsion parameter of the target heart may comprise: determining speckles in the preset segment in the region of interest, and performing motion tracking on the speckles to obtain a rotation parameter of the preset segment of the target heart.

In an embodiment, the performing, by the processor 40, motion tracking on the region of interest, so as to obtain a reliability of the torsion parameter may comprise: determining speckles in the preset segment in the region of interest; performing motion tracking on the speckles to obtain image quality and a tracking result corresponding to the preset segment; and determining a reliability of the rotation parameter of the preset segment according to the image quality and the tracking result corresponding to the preset segment. A reliability of a rotation parameter of any segment is positively correlated with image quality and a tracking result corresponding to the segment. Better image quality and a better tracking result corresponding to the segment indicates a higher reliability of the rotation parameter of the segment. The image quality may be defined in terms of resolution, sharpness, noise, frame rate, etc. of the ultrasound image. For example, higher resolution, better sharpness, smaller noise, and a higher frame rate of the ultrasound image indicates better image quality. The tracking result may be the consistency of the motion tracking on the speckles. This consistency may be calculated by using a variance of a local motion vector. The consistency of motion tracking is inversely correlated with the variance of the local motion vector. A smaller variance of the local motion vector indicates better consistency of motion tracking. For example, after the speckles in the preset segment in the region of interest are determined, motion vectors of these speckles are calculated, and then the variance of these motion vectors is calculated. A smaller variance indicates better consistency of the motion tracking on the preset segment.

In an embodiment, after the rotation parameter of the preset segment and the confidence thereof are obtained, they may be displayed by the display 50.

In an embodiment, the displaying the torsion parameter by the display 50 may comprise: displaying the rotation parameter of the preset segment in the form of a curve graph, where the preset segment is identified in the curve graph by at least one of a color (color coding), a pattern, and a character. In an embodiment, a curve graph on a rotation parameter of any segment may be generated from the rotation parameter of the segment and a detection time of a view frame corresponding thereto.

In an embodiment, the displaying, by the display 50, the reliability of the torsion parameter may comprise: displaying a structure icon corresponding to the preset segment, where the preset segment is identified in the structure icon by at least one of color coding, a pattern, and a character; and displaying a reliability of the rotation parameter of the preset segment on the structure icon. In an embodiment, the structure icon may be an icon having a typical structure of a segment, so that the segment may be represented by the structure icon, and therefore a user can know the segment represented by the structure icon from the structure icon. In an embodiment, displaying, by the display 50, the reliability of the rotation parameter of the preset segment on the structure icon comprises: displaying the reliability of the rotation parameter of the preset segment on a boundary of the structure icon corresponding to the preset segment by at least one of a color, a pattern, and a character. For example, a color-coded boundary is taken as an example, a color of the boundary of the structure icon corresponding to the preset segment represents the reliability of the rotation parameter of the preset segment, and different colors represent values of different reliabilities. To make it easier for a user to understand a reliability represented by the current color, a color bar may be displayed in a nearby area. Different colors in the color bar represent values of different reliabilities, so that the user can obtain the reliability of the rotation parameter of the preset segment with reference to the color bar and the color of the boundary of the preset segment on the structure icon. Similarly, a pattern is taken as an example. When the boundary of the corresponding preset segment on the structure icon is identified by a pattern, different patterns represent values of different reliabilities. Similarly, a character is taken as an example. When the boundary of the corresponding preset segment on the structure icon is identified by a character, different characters represent different values of reliabilities. For example, the character may be a number, and the value of the number represents the value of a reliability.

Figure 2:
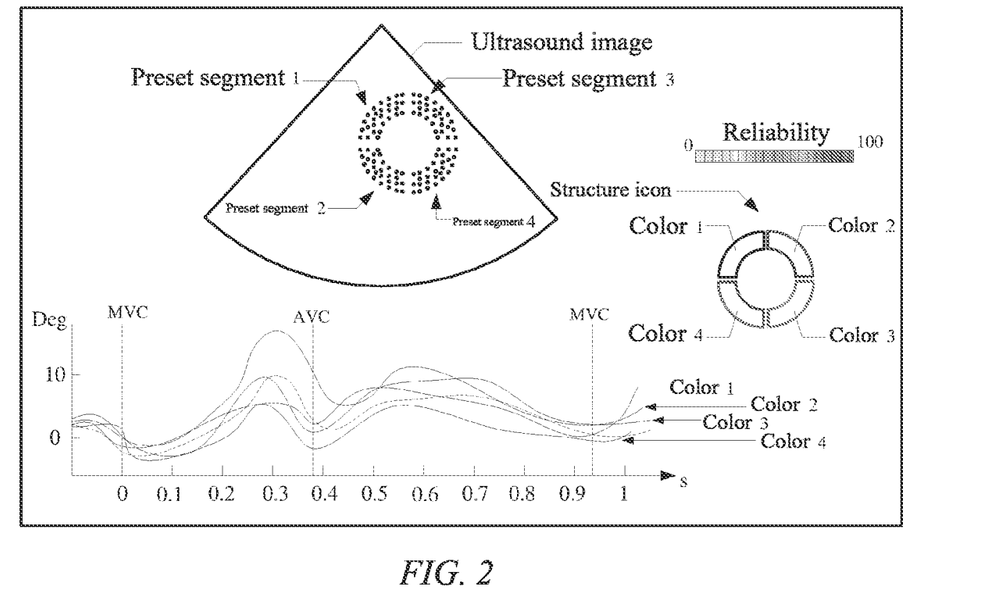
FIG. 2 shows an example of displaying an ultrasound image, a region of interest, a rotation parameter of a preset segment, and a reliability of the rotation parameter of the preset segment.

In the display 50, the curve graph and the structure icon of the preset segment may both identify the preset segment by at least one of color coding, a pattern, and a character, so that a user can easily associate the curve graph and the structure icon of the same segment, and can clearly know which curve graph corresponds to which structure icon. Taking a color as an example, a curve graph and a structure icon that are coded by the same color correspond to the same segment; taking a pattern as an example, a curve graph and a structure icon identified by the same pattern correspond to the same segment; and taking a character as an example, a curve graph and a structure icon identified by the same character correspond to the same segment, for example, the character may be text. In addition, when the display 50 further displays an ultrasound image and a region of interest, a user can clearly know which structure icon corresponds to which segment on the ultrasound image according to the consistency between the a structure icon of a segment and a segment of an actually displayed ultrasound image, and because the user knows which structure icon corresponds to which curve graph, the user can clearly know which curve graph corresponds to which segment on the ultrasound image. With reference to all these, the user can associate image information on the ultrasound image with a quantitative parameter, know which segment on the ultrasound image corresponds to which curve graph and which structure icon, and read a corresponding rotation parameters and a reliability of the rotation parameter. FIG. 2 shows an example in which black dots in an ultrasound image are speckles determined in a region of interest, and a structure icon on the right side of a display interface comprises four preset segments, which are respectively filled with a color 1, a color 2, a color 3, and a color 4. The user can clearly know which structure icon corresponds to which segment in the ultrasound image according to the consistency between the speckles of the segments in the ultrasound image and the structure icon. For example, a preset segment 1 in the ultrasound image corresponds to the segment filled with the color 1 in the structure icon, a preset segment 2 in the ultrasound image corresponds to the segment filled with the color 2 in the structure icon, a preset segment 3 in the ultrasound image corresponds to the segment filled with the color 3 in the structure icon, and the preset segment 4 in the ultrasound image corresponds to the segment filled with the color 4 in the structure icon. Boundaries of the four segments in the structure icon are all color-coded to correspond to values of a reliability color bar, that is, a boundary color of the structure icon of the preset segment 1 represents a reliability of a rotation parameter of the preset segment 1; a boundary color of the structure icon of the preset segment 2 represents a reliability of a rotation parameter of the preset segment 2; a boundary color of the structure icon of the preset segment 3 represents a reliability of a rotation parameter of the preset segment 3; and a boundary color of the structure icon of the preset segment 4 represents a reliability of a rotation parameter of the preset segment 4. A curve graph at the bottom of the display interface represents the rotation parameters of the preset segments, where the abscissa is time, and the ordinate is angle; A curve of the rotation parameter of the segment filled with the color 1 in the structure icon is a curve of the color 1; a curve of the rotation parameter of the segment filled with the color 2 in the structure icon is a curve of color 2; a curve of the rotation parameter of the segment filled with the color 3 in the structure icon is a curve of the color 3; and a curve of the rotation parameter of the segment filled with the color 4 in the structure icon is a curve of the color 4. A dashed curve in the curve graph represents the left ventricular torsion parameter. Those skilled in the art can understand that the curves in FIG. 2 have different angles at various moments, which is only used as an example rather than a limitation. In the figure, MVC represents mitral valve closure, and AVC represents aortic valve closure.

Considering the intuitiveness and convenience of interaction, in an embodiment, the processor 40 can receive a segment selection instruction for the preset segment corresponding to the structure icon, and determine a selected segment according to the segment selection instruction. For example, a user may select a segment by using input tools such as a mouse and a keyboard, i.e., input a segment selection instruction for the preset segment corresponding to the structure icon. If the display 50 is a touch display screen, the user can also directly select a segment on the display 50 with a finger or the like, i.e., input a segment selection instruction for the preset segment corresponding to the structure icon. The display 50 may perform one or more of the following (1), (2), and (3):

(1) The selected segment is highlighted on the structure icon. In an embodiment, the highlighting, by the display 50, the selected segment on the structure icon may comprise: highlighting the selected segment on the structure icon in a highlighted and/or bold manner; or displaying the selected segment, and hiding an unselected segment.

(2) A rotation parameter of the selected segment is highlighted on the curve graph. In an embodiment, the highlighting, by the display 50, a rotation parameter of the selected segment on the curve graph may comprise: highlighting a rotation parameter curve of the selected segment in a highlighted and/or bold manner; or displaying a rotation parameter curve of the selected segment; and hiding a rotation parameter curve of an unselected segment.

(3) The selected segment is highlighted in a corresponding region of interest in the ultrasound image. In an embodiment, the highlighting, by the display 50, the selected segment in a corresponding region of interest in the ultrasound image may comprise: highlighting the selected segment in a corresponding region of interest in the ultrasound image in a highlighted and/or bold manner; or displaying speckles in a region of interest that is in the ultrasound image and corresponds to the selected segment, and hiding speckles in a region of interest that is in the ultrasound image and corresponds to an unselected segment.

The foregoing are some embodiments in which the rotation parameter of the preset segment is displayed by using a curve graph, and the reliability of the rotation parameter of the preset segment is displayed by identifying the boundary of the structure icon, and the like.

In some other embodiments, the display 50 may further display rotation parameters of all preset segments and reliabilities of the rotation parameters of all the preset segments by using a curve graph. In an embodiment, the processor further receives an invalidation selection instruction for the preset segments, and removes a selected invalid segment from the preset segments according to the invalidation selection instruction. For example, the user may select invalid segments by using input tools such as a mouse and a keyboard, i.e., input the invalidation selection instructions for all the preset segments. If the display 50 is a touch display screen, the user can also directly select invalid segments on the display 50 with a finger or the like, i.e., input the invalidation selection instructions for the preset segments. The display 50 displays rotation parameters of valid segments and reliabilities of the rotation parameters of the valid segments by using a curve graph, where the valid segments are segments of the preset segments other than the invalid segments. In an embodiment, the rotation parameters of the invalid segments do not participate in the calculation of the left ventricular torsion parameter. In an embodiment, the reliabilities of the rotation parameters of the invalid segments do not participate in the calculation of the reliability of the left ventricular torsion parameter.

Figure 3:
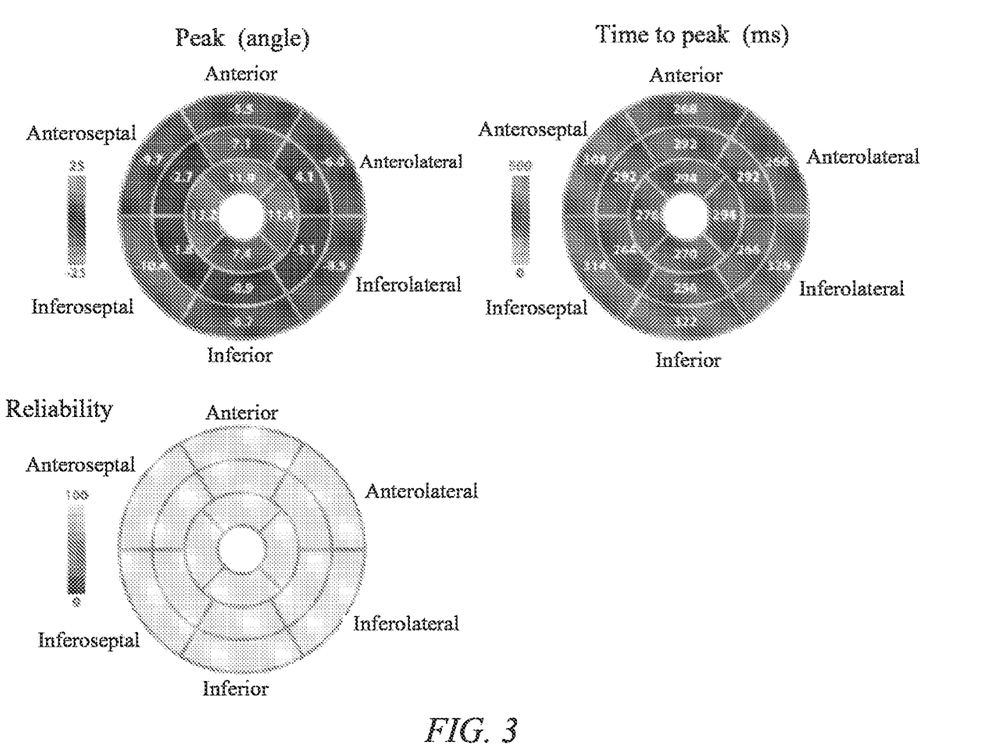
FIG. 3 shows an example of displaying information such as a rotation parameter of a preset segment and a reliability of the rotation parameter of the preset segment.

In addition, a bull's eye plot may further be introduced to display related parameters. For example, in an embodiment, the displaying, by the display 50, the torsion parameter and the reliability of the torsion parameter may comprise: displaying the rotation parameter of the preset segment and a reliability of the rotation parameter of the preset segment by using a bull's eye plot. To enable the user to obtain more information by using the display 50, in an embodiment, the display 50 further displays, by using a bull's eye plot, a peak value of the rotation parameter of the preset segment and/or a time spent for the rotation parameter of the preset segment to reach the peak value (time to peak). FIG. 3 shows an example in which a bull's eye plot in the upper left corner provides information about a peak value of a rotation parameter of a preset segment; a bull's eye plot in the upper right corner provides information about a time spent for the rotation parameter of the preset segment to reach the peak value; and a bull's eye plot in the lower left corner provides information about a value of a reliability of the rotation parameter of the preset segment.

The following describes the calculation and display of the left ventricular torsion parameter of the heart and the confidence thereof.

In an embodiment, the left ventricular torsion parameter may be obtained based on the rotation parameter of the preset segment. For example, the left ventricular torsion parameter may be obtained based on rotation parameters of two preset segments, i.e., a horizontal short-axial section of the mitral valve (PSAXB) and a short-axis section of the apex (PSAXAP). The left ventricular torsion parameter may be obtained by subtracting the rotation parameter of the preset segment of the horizontal short-axial section of the mitral valve from the rotation parameter of the preset segment of the short-axis section of the apex.

In an embodiment, the reliability of the left ventricular torsion parameter is obtained based on the reliability of the rotation parameters of the preset segment. For example, the reliability of the left ventricular torsion parameter may be obtained based on reliabilities of the rotation parameters of the two preset segments, i.e., the horizontal short-axial section of the mitral valve and the short-axis section of the apex. In specific calculation, the reliability of the left ventricular torsion parameter is the average, minimum, maximum, etc. of the reliabilities of the rotation parameters of related preset segments (such as the horizontal short-axis section of the mitral valve and the short-axis section of the apex).

Figure 4:
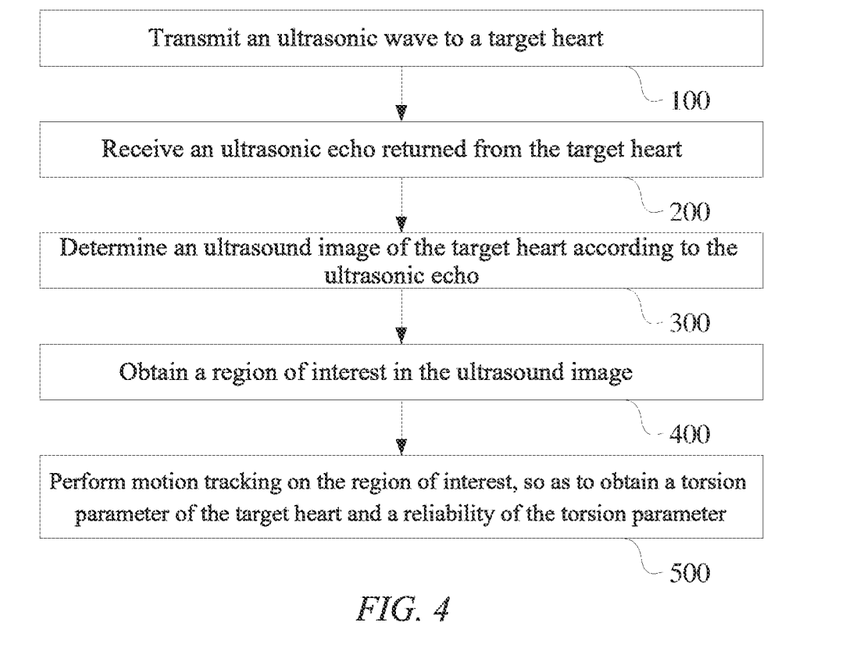
FIG. 4 is a flow chart of a quantitative analysis method for cardiac motion according to an embodiment.
Figure 5:
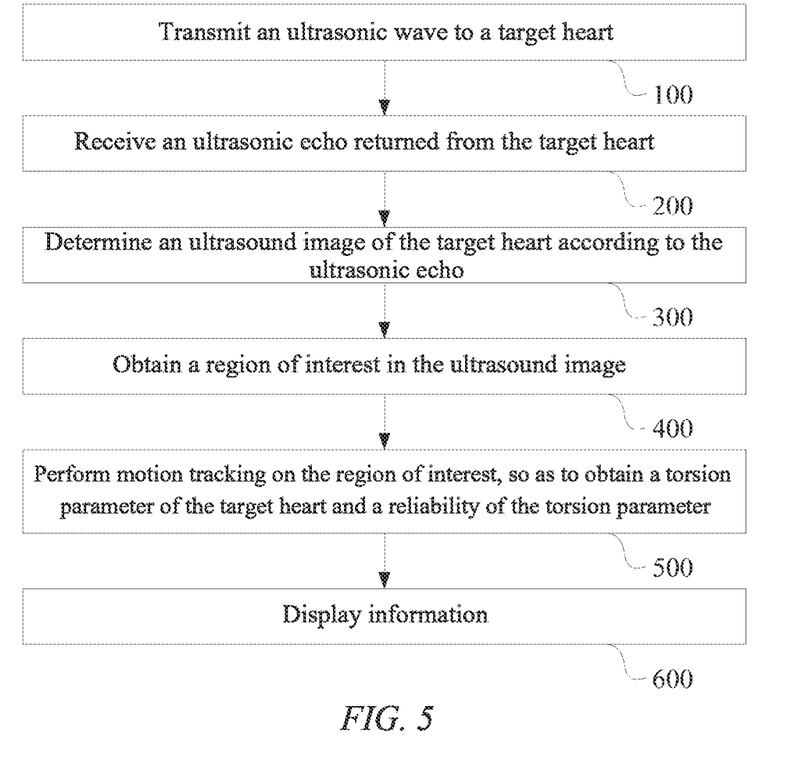
FIG. 5 is a flow chart of a quantitative analysis method for cardiac motion according to another embodiment.

The ultrasonic system of the disclosure has been described above with reference to a plurality of embodiments. Referring to FIG. 4 and FIG. 5, an embodiment of the disclosure further discloses a quantitative analysis method for cardiac motion, comprising step 100 to step 500, and in an embodiment, the method may further comprise step 600. Details will be described below.

At step 100, an ultrasonic wave is transmitted to a target heart.

At step 200, an ultrasonic echo returned from the target heart is received.

At step 300, an ultrasound image of the target heart is determined according to the ultrasonic echo.

At step 400, an region of interest in the ultrasound image is obtained. The region of interest may be preset or may be input by a user. For example, the user selects the region of interest in the ultrasound image by using a mouse, a keyboard, etc.

Figure 6:
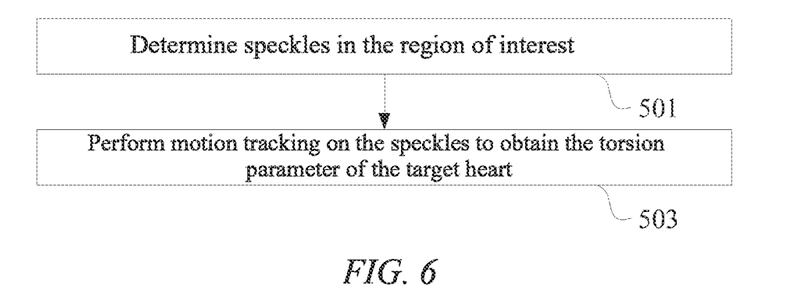
FIG. 6 is a flow chart of performing motion tracking on a region of interest to obtain a torsion parameter of a target heart according to an embodiment.

At step 500, motion tracking is performed on the region of interest, so as to obtain a torsion parameter of the target heart and a reliability of the torsion parameter. Referring to FIG. 6, in an embodiment, step 500 of performing motion tracking on the region of interest, so as to obtain a torsion parameter of the target heart may comprise step 501 and step 503. At step 501, speckles in the region of interest are determined. At step 503, motion tracking is performed on the speckles to obtain the torsion parameter of the target heart.

The following describes the torsion parameter of the heart and the reliability thereof.

The torsion parameter of the heart is a parameter about the torsional motion of the heart. In an embodiment, the torsion parameter of the heart may comprise a global torsion parameter and/or a local torsion parameter. The global torsion parameter is a parameter used to globally describe the torsional motion of the heart, such as a left ventricular torsion parameter. The local torsion parameter is a parameter used to describe the torsional motion of the heart from various parts of the heart, such as a rotation parameter of a preset segment. The preset segment of the heart may comply with the division of standard segments defined by an ultrasound industry standards association, or may be defined by a user himself or herself. In an embodiment, the left ventricular torsion parameter may be obtained based on a rotation parameter of the preset segment. For example, the left ventricular torsion parameter may be obtained based on rotation parameters of two segments, i.e., the apex and the base.

The reliability of the torsion parameter of the heart is used to quantify the reliability and accuracy of the torsion parameter. The torsion parameter of the heart comprises the global torsion parameter and/or the local torsion parameter, and accordingly, the reliability of the torsion parameter of the heart may comprise a reliability for quantitative evaluation of the global torsion parameter and a reliability for quantitative evaluation of the local torsion parameter, such as a reliability of the left ventricular torsion parameter and/or a reliability of the rotation parameter of preset segment. In an embodiment, the reliability of the left ventricular torsion parameter is obtained based on a reliability of the rotation parameter of the preset segment. For example, the reliability of the left ventricular torsion parameter may be obtained based on the reliability of the rotation parameters of the two segments, i.e., the apex and the base.

The following describes the calculation of the rotation parameter of the preset segment of the heart.

Figure 7:
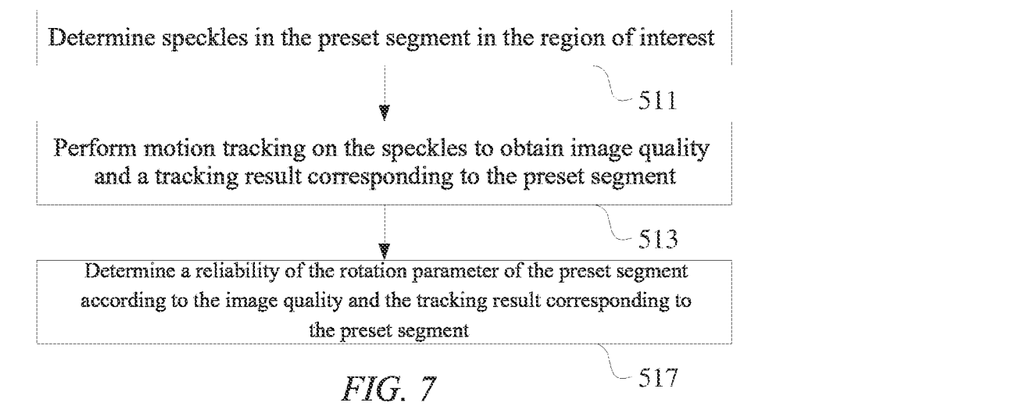
FIG. 7 is a flow chart of performing motion tracking on a region of interest to obtain a reliability of a torsion parameter according to an embodiment.

Referring to FIG. 7, in an embodiment, step 500 of performing motion tracking on the region of interest, so as to obtain a reliability of the torsion parameter may comprise step 511 to step 515.

At step 511, speckles in the preset segment in the region of interest are determined.

At step 513, motion tracking is performed on the speckles to obtain image quality and a tracking result corresponding to the preset segment.

At step 515, a reliability of the rotation parameter of the preset segment is determined according to the image quality and the tracking result corresponding to the preset segment.

A reliability of a rotation parameter of any segment is positively correlated with image quality and a tracking result corresponding to the segment. Better image quality and a better tracking result corresponding to the segment indicates a higher reliability of the rotation parameter of the segment. The image quality may be defined in terms of resolution, sharpness, noise, frame rate, etc. of the ultrasound image. For example, higher resolution, better sharpness, smaller noise, and a higher frame rate of the ultrasound image indicates better image quality. The tracking result may be the consistency of the motion tracking on the speckles. This consistency may be calculated by using a variance of a local motion vector. The consistency of motion tracking is inversely correlated with the variance of the local motion vector. A smaller variance of the local motion vector indicates better consistency of motion tracking. For example, after the speckles in the preset segment in the region of interest are determined, motion vectors of these speckles are calculated, and then the variance of these motion vectors is calculated. A smaller variance indicates better consistency of the motion tracking on the preset segment.

At step 600, information is displayed. In step 600, one or both of the following (1) and (2) may be displayed: (1) the ultrasound image and the region of interest; and (2) the torsion parameter and the reliability of the torsion parameter. Detailed description is given below.

In an embodiment, step 600 of displaying the torsion parameter may comprise: displaying the rotation parameter of the preset segment in the form of a curve graph, where the preset segment is identified in the curve graph by at least one of color coding, a pattern, and a character. In an embodiment, a curve graph on a rotation parameter of any segment may be generated from the rotation parameter of the segment and a detection time of a view frame corresponding thereto.

In an embodiment, step 600 of displaying the reliability of the torsion parameter may comprise: displaying a structure icon corresponding to the preset segment, where the preset segment is identified in the structure icon by at least one of color coding, a pattern, and a character; and displaying a reliability of the rotation parameter of the preset segment on the structure icon. In an embodiment, step 600 of displaying a reliability of the rotation parameter of the preset segment on the structure icon comprises: displaying the reliability of the rotation parameter of the preset segment on a boundary of the structure icon corresponding to the preset segment by at least one of a color, a pattern, and a character. For example, a color-coded boundary is taken as an example, a color of the boundary of the corresponding preset segment on the structure icon represents the reliability of the rotation parameter of the preset segment, and different colors represent values of different reliabilities. To make it easier for a user to understand a reliability represented by the current color, a color bar may be displayed in a nearby area. Different colors in the color bar represent values of different reliabilities, so that the user can obtain the reliability of the rotation parameter of the preset segment with reference to the color bar and the color of the boundary of the preset segment on the structure icon. Similarly, a pattern is taken as an example. When the boundary of the corresponding preset segment on the structure icon is identified by a pattern, different patterns represent values of different reliabilities. Similarly, a character is taken as an example. When the boundary of the corresponding preset segment on the structure icon is identified by a character, different characters represent different values of reliabilities. For example, the character may be a number, and the value of the number represents the value of a reliability.

In the display mode of the above embodiments, the curve graph and the structure icon of the preset segment may both identify the preset segment by at least one of color coding, a pattern, and a character, so that a user can easily associate the curve graph and the structure icon of the same segment, and can clearly know which curve graph corresponds to which structure icon. Taking a color as an example, a curve graph and a structure icon that are coded by the same color correspond to the same segment; taking a pattern as an example, a curve graph and a structure icon identified by the same pattern correspond to the same segment; and taking a character as an example, a curve graph and a structure icon identified by the same character correspond to the same segment, for example, the character may be text. In addition, when an ultrasound image and a region of interest are further displayed in step 600, a user can clearly know which structure icon corresponds to which segment on the ultrasound image according to the consistency between the a structure icon of a segment and a segment of an actually displayed ultrasound image, and because the user knows which structure icon corresponds to which curve graph, the user can clearly know which curve graph corresponds to which segment on the ultrasound image. With reference to all these, the user can associate image information on the ultrasound image with a quantitative parameter, know which segment on the ultrasound image corresponds to which curve graph and which structure icon, and read a corresponding rotation parameters and a reliability of the rotation parameter. For a specific example, reference may be made back to FIG. 2 and the description thereof, which will not be repeated herein.

Figure 8:
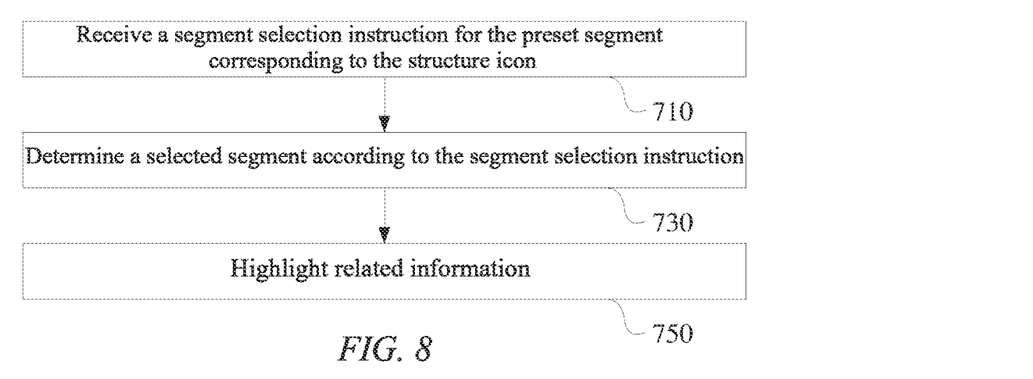
FIG. 8 is a flow chart of a quantitative analysis method for cardiac motion according to still another embodiment.

Considering the intuitiveness and convenience of interaction, referring to FIG. 8, in an embodiment, the quantitative analysis method for cardiac motion further comprises step 710 to step 750.

At step 710, a segment selection instruction for the preset segment corresponding to the structure icon is received. For example, a user may select a segment by using a mouse, a keyboard, a touch display screen or the like, i.e., input a segment selection instruction for the preset segment corresponding to the structure icon.

At step 730, a selected segment is determined according to the segment selection instruction.

At step 750, related information is highlighted. Step 750 may comprise one or more of the following (1), (2) and (3):
(1) The selected segment is highlighted on the structure icon. In an embodiment, step 750 of highlighting the selected segment on the structure icon may comprise: highlighting the selected segment on the structure icon in a highlighted and/or bold manner; or displaying the selected segment, and hiding an unselected segment.
(2) A rotation parameter of the selected segment is highlighted on the curve graph. In an embodiment, step 750 of highlighting a rotation parameter of the selected segment on the curve graph may comprise: highlighting a rotation parameter curve of the selected segment in a highlighted and/or bold manner; or displaying a rotation parameter curve of the selected segment; and hiding a rotation parameter curve of an unselected segment.
(3) The selected segment is highlighted in a corresponding region of interest in the ultrasound image. In an embodiment, step 750 of highlighting the selected segment in a corresponding region of interest in the ultrasound image may comprise: highlighting the selected segment in a corresponding region of interest in the ultrasound image in a highlighted and/or bold manner; or displaying speckles in a region of interest that is in the ultrasound image and corresponds to the selected segment, and hiding speckles in a region of interest that is in the ultrasound image and corresponds to an unselected segment.

The foregoing are some embodiments in which the rotation parameter of the preset segment is displayed by using a curve graph, and the reliability of the rotation parameter of the preset segment is displayed by identifying the boundary of the structure icon, and the like.

Figure 9:
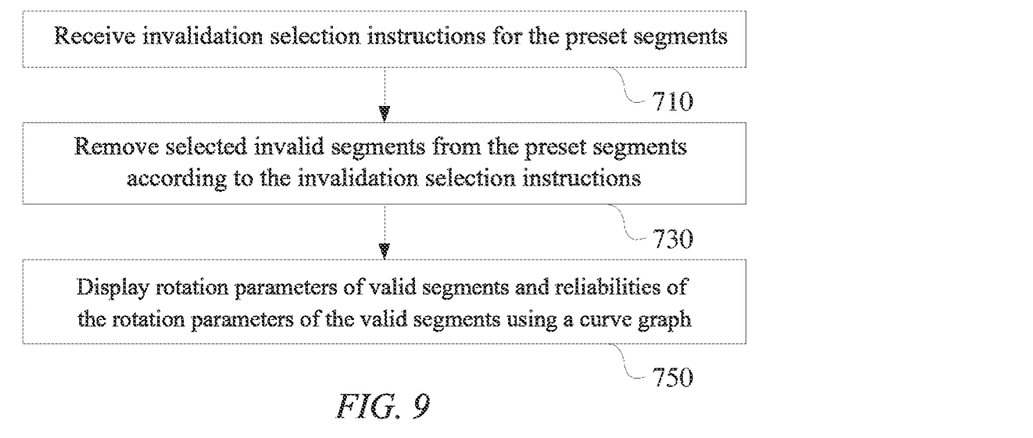
FIG. 9 is a flow chart of a quantitative analysis method for cardiac motion according to yet another embodiment.

In some other embodiments, at step 600, rotation parameters of all preset segments and reliabilities of the rotation parameters of all the preset segments may further be displayed by using a curve graph. Operations on these curve graphs may further be provided. Referring to FIG. 9, in an embodiment, the quantitative analysis method for cardiac motion may further comprise step 810 to step 850.

At step 810, the invalidation selection instructions for all the preset segments are received. For example, the user may select invalid segments by using tools such as a mouse, a keyboard, and a touch display screen, i.e., input the invalidation selection instructions for the preset segments.

At step 830, selected invalid segments are removed from the preset segments according to the invalidation selection instructions.

At step 850, rotation parameters of valid segments and reliabilities of the rotation parameters of the valid segments are displayed by using a curve graph, where the valid segments are segments of the preset segments other than the invalid segments.

In an embodiment, the rotation parameters of the invalid segments do not participate in the calculation of the left ventricular torsion parameter. In an embodiment, the reliabilities of the rotation parameters of the invalid segments do not participate in the calculation of the reliability of the left ventricular torsion parameter.

In addition, a bull's eye plot may further be introduced to display related parameters. For example, in an embodiment, step 600 of displaying the torsion parameter and the reliability of the torsion parameter may comprise: displaying the rotation parameter of the preset segment and a reliability of the rotation parameter of the preset segment by using a bull's eye plot. To enable the user to obtain more information, in an embodiment, at step 600, a peak value of the rotation parameter of the preset segment and/or a time spent for the rotation parameter of the preset segment to reach the peak value are further displayed by using a bull's eye plot. For a specific example, reference may be made back to FIG. 3 and the description thereof, which will not be repeated herein.

The above is the description of several embodiments of the quantitative analysis method for cardiac motion and the ultrasonic system proposed in the disclosure. In the disclosure, during the quantitative analysis of the torsional motion of the heart, the reliability of the analysis result is also provided, that is, quantitative evaluation is also performed on the analysis result, which may assist a physician in making a more accurate cardiac function evaluation.

The description has been made with reference to various exemplary embodiments herein. However, those skilled in the art would have appreciated that changes and modifications could have been made to the exemplary embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In the above embodiments, the disclosure may be implemented in whole or in part by software, hardware, firmware, or any combination thereof. In addition, as understood by those skilled in the art, the principles herein may be reflected in a computer program product on a computer-readable storage medium that is pre-installed with computer-readable program codes. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions can be loaded onto a general-purpose computer, a dedicated computer, or other programmable data processing device to form a machine, such that these instructions executed on a computer or other programmable data processing apparatus can generate an apparatus that implements a specified function. These computer program instructions can also be stored in a computer-readable memory that can instruct a computer or other programmable data processing device to operate in a specific manner, such that the instructions stored in the computer-readable memory can form a manufactured product, including an implementation apparatus that implements a specified function. The computer program instructions can also be loaded onto a computer or other programmable data processing device, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, those skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

Those skilled in the art will recognize that many changes can be made to the details of the above-described embodiments without departing from the basic principles of the disclosure. Therefore, the scope of the disclosure should be determined only by the claims as follows.

The invention claimed is:

1. A quantitative analysis method for cardiac motion, comprising:
    transmitting an ultrasonic wave to a target heart;
    receiving an ultrasonic echo returned from the target heart;
    determining an ultrasound image of the target heart according to the ultrasonic echo;
    obtaining a region of interest in the ultrasound image;
    performing motion tracking on the region of interest to obtain a torsion parameter of the target heart and a reliability of the torsion parameter, wherein the target heart is divided into multiple preset segments and the torsion parameter comprises rotation parameters of the multiple preset segments; and
    displaying the rotation parameters of the multiple preset segments and reliabilities of the rotation parameters of the multiple preset segments.

2. The quantitative analysis method for cardiac motion of claim 1, further comprising: displaying the ultrasound image and the region of interest.

3. The quantitative analysis method for cardiac motion of claim 1, wherein performing the motion tracking on the region of interest to obtain the torsion parameter of the target heart comprises:
    determining a speckle in the region of interest; and
    performing the motion tracking on the speckle to obtain the torsion parameter of the target heart.

4. The quantitative analysis method for cardiac motion of claim 1, wherein performing the motion tracking on the region of interest to obtain the reliability of the torsion parameter comprises:
    determining a speckle in each of the multiple preset segments in the region of interest;
    performing the motion tracking on the speckle to obtain an image quality and a tracking result corresponding to the preset segment; and
    determining a reliability of the rotation parameter of the preset segment according to the image quality and the tracking result corresponding to the preset segment.

5. The quantitative analysis method for cardiac motion of claim 1, wherein displaying the rotation parameters of the multiple preset segments comprises:
    displaying the rotation parameters of the multiple preset segments in a form of a curve graph, wherein each of the multiple preset segments is identified in the curve graph by at least one of a color, a pattern and a character.

6. The quantitative analysis method for cardiac motion of claim 1, wherein displaying the reliabilities of the rotation parameters of the multiple preset segments comprises:
    displaying a structure icon corresponding to the multiple preset segments, wherein each of the multiple preset segments is identified in the structure icon by at least one of a color, a pattern and a character; and
    displaying the reliabilities of the rotation parameters of the multiple preset segments on the structure icon.

7. The quantitative analysis method for cardiac motion of claim 6, wherein displaying the reliabilities of the rotation parameters of the multiple preset segments on the structure icon comprises:
    displaying a reliability of a rotation parameter of each of the multiple preset segments on a boundary of the structure icon corresponding to the multiple preset segments by at least one of a color, a pattern and a character.

8. The quantitative analysis method for cardiac motion of claim 6, further comprising:
    receiving a segment selection instruction for the multiple preset segments corresponding to the structure icon;
    determining a selected segment according to the segment selection instruction; and
    highlighting the selected segment on the structure icon.

9. The quantitative analysis method for cardiac motion of claim 8, further comprising: highlighting a rotation parameter of the selected segment on a curve graph.

10. The quantitative analysis method for cardiac motion of claim 8, further comprising: highlighting the selected segment in the region of interest in the ultrasound image.

11. The quantitative analysis method for cardiac motion of claim 8, wherein highlighting the selected segment on the structure icon comprises:
    highlighting the selected segment on the structure icon in a highlighted manner and/or a bold manner; or
    displaying the selected segment and hiding an unselected segment.

12. The quantitative analysis method for cardiac motion of claim 9, wherein highlighting the rotation parameter of the selected segment on the curve graph comprises:
    highlighting a rotation parameter curve of the selected segment in a highlighted manner and/or a bold manner; or
    displaying a rotation parameter curve of the selected segment and hiding a rotation parameter curve of an unselected segment.

13. The quantitative analysis method for cardiac motion of claim 10, wherein highlighting the selected segment in the region of interest in the ultrasound image comprises:
    highlighting the selected segment in the region of interest in the ultrasound image in a highlighted manner and/or a bold manner; or
    displaying a speckle in the region of interest in the ultrasound image corresponding to the selected segment and hiding a speckle in the region of interest in the ultrasound image corresponding to an unselected segment.

14. The quantitative analysis method for cardiac motion of claim 1, wherein the torsion parameter comprises a left ventricular torsion parameter, wherein the left ventricular torsion parameter is obtained based on a rotation parameter of a preset segment, and a reliability of the left ventricular torsion parameter is obtained based on a reliability of the rotation parameter of the preset segment.

15. The quantitative analysis method for cardiac motion of claim 14, wherein displaying the rotation parameters of the multiple preset segments and the reliabilities of the rotation parameters of the multiple preset segments comprises:
    displaying the rotation parameters of all of the multiple preset segments and the reliabilities of the rotation parameters of all of the multiple preset segments using curve graphs.

16. The quantitative analysis method for cardiac motion of claim 15, further comprising:
    receiving an invalidation selection instruction for all of the multiple preset segments;
    removing a selected invalid segment from all of the multiple preset segments according to the invalidation selection instruction; and
    displaying a rotation parameter of a valid segment and a reliability of the rotation parameter of the valid segment using a curve graph, wherein the valid segment is a segment of all of the multiple preset segments excluding the selected invalid segment.

17. The quantitative analysis method for cardiac motion of claim 1, wherein displaying the rotation parameters of the multiple preset segments and the reliabilities of the rotation parameters of the multiple preset segments comprises:
    displaying the rotation parameters of the multiple preset segments and the reliabilities of the rotation parameters of the multiple preset segments with a bull's eye plot.

18. The quantitative analysis method for cardiac motion of claim 17, further comprising:
    displaying, with the bull's eye plot, a peak value of a rotation parameter of each of the multiple preset segments and/or a time for the rotation parameter of the preset segment to reach the peak value.

* * * * *